(12) United States Patent
Kuramori et al.

(10) Patent No.: US 8,195,284 B2
(45) Date of Patent: Jun. 5, 2012

(54) BIOELECTRICAL INFORMATION ACQUISITION DEVICE AND INAPPROPRIATELY-ATTACHED-ELECTRODE IDENTIFYING METHOD

(75) Inventors: Akira Kuramori, Kanagawa (JP); Masayoshi Kamijo, Nagano (JP); Tsugutake Sadoyama, Nagano (JP)

(73) Assignee: The Yokohoma Rubber Co., Ltd., Tokyo (JP)

( * ) Notice: Subject to any disclaimer, the term of this patent is extended or adjusted under 35 U.S.C. 154(b) by 888 days.

(21) Appl. No.: 12/160,293

(22) PCT Filed: Jan. 25, 2007

(86) PCT No.: PCT/JP2007/051141
§ 371 (c)(1),
(2), (4) Date: Jul. 8, 2008

(87) PCT Pub. No.: WO2007/086448
PCT Pub. Date: Aug. 2, 2007

(65) Prior Publication Data
US 2009/0012381 A1    Jan. 8, 2009

(30) Foreign Application Priority Data
Jan. 27, 2006  (JP) .................. 2006-019547

(51) Int. Cl.
*A61B 5/05* (2006.01)
(52) U.S. Cl. ...................................... 600/547
(58) Field of Classification Search .......... 600/547, 600/546, 509
See application file for complete search history.

(56) References Cited

U.S. PATENT DOCUMENTS

| | | | |
|---|---|---|---|
| 3,732,859 A | 5/1973 | Tateno |
| 4,279,258 A | 7/1981 | John |
| 5,042,498 A | 8/1991 | Dukes |
| 6,076,011 A | 6/2000 | Hoover |
| 2003/0083584 A1 | 5/2003 | Yonce |

FOREIGN PATENT DOCUMENTS

| | | |
|---|---|---|
| GB | 2162342 | 1/1986 |
| JP | 63-314473 | 12/1988 |
| JP | 04-227229 | 8/1992 |
| JP | 06-154181 | 6/1994 |
| JP | 1998-195268 | 12/1998 |
| JP | 2002-125948 | 5/2002 |

OTHER PUBLICATIONS

Supplementary European Search Report, dated Feb. 25, 2009.
Euopean Office Action dated Feb. 28, 2011 for counterpart European Application No. 07707388.0.

*Primary Examiner* — Max Hindenburg
*Assistant Examiner* — Megan Leedy
(74) *Attorney, Agent, or Firm* — Knobbe Martens Olson & Bear LLP (57) ABSTRACT

A plurality of electrode pairs, each of which is constituted by two electrodes of the plurality of biomedical electrodes are set and at least one of an electrical impedance value between two electrodes forming a pair and a resistance value between the two electrodes, for each of the electrode pairs is measured. An attachment state of each of the electrode pairs is judged by comparing the impedance value or the resistance value with a predetermined range of numeric values. An electrode in an inappropriate attachment state is identified from the plurality of electrode pairs based on the judged attachment state o each of the plurality of electrode pairs.

12 Claims, 4 Drawing Sheets

BIOELECTRICAL INFORMATION ACQUISITION DEVICE AND INAPPROPRIATELY-ATTACHED-ELECTRODE IDENTIFYING METHOD

CROSS REFERENCE TO RELATED APPLICATION

This application claims the benefit and priority to and is a U.S. National Phase of PCT International Application Number PCT/JP2007/051141, filed on Jan. 25, 2007, designating the United States of America, which claims priority under 35 U.S.C. §119 to Japanese Application Number 2006-019547 filed on Jan. 27, 2006. The disclosures of the above-described applications are hereby incorporated by reference in their entireties.

BACKGROUND OF THE INVENTION

1. Field of the Invention

The present invention relates to a bioelectrical information acquisition device for obtaining bioelectrical information on a human body, such as electromyographic information or electrocardiographic information, through a plurality of electrodes attached to the human body. In particular, the present invention provides a bioelectrical information acquisition device and an inappropriately-attached-electrode identifying method which are capable of identifying, of a plurality of electrodes, an electrode which is inappropriately attached.

2. Description of the Related Art

In measuring bioelectrical information, such as, in electrocardiographic measurement or in electromyographic measurement, a biomedical electrode and a bio amp are generally used. The biomedical electrode is fixed onto skin with adhesive tape or the like, through which a feeble change in potential on the skin surface resulting from a heartbeat or from an action of the human body is detected, and the change is measured. In general, a feeble change in potential (several μV to several mV) derived by the electrode is amplified by the bio amp by several hundred to several thousand times, so as to be a signal that can be handled by common electronic equipment.

There exists an electric impedance between the biomedical electrode and the skin. The value of this electric impedance changes depending on how the electrode is attached to the skin (a contact state between the skin and the electrode). In measuring bioelectrical information, if the variation of the impedance is large, noise components (potential variations) resulting from the variation of the impedance are increased, with the result that a sufficient measurement accuracy (S/N ratio) cannot be obtained. In other words, in the case where an attachment state of the electrode (a contact state between the skin and the electrode) is not constant (in the case where an inappropriate attachment state is caused in the electrode), the bioelectrical information cannot be obtained with a sufficient measurement accuracy (S/N ratio). Further, if the electrode has peeled off, it is of course impossible to carry out the measurement.

Patent Document 1 mentioned below discloses a portable electrocardiographic monitor which allows a person to measure own electrocardiography. The portable electrocardiographic monitor according to Patent Document 1 includes a second measurement electrode disposed at a position which comes into contact with a hand of the person when the person holds the portable electrocardiographic monitor by hands, and a first measurement electrode is disposed on a main body part on which the second measurement electrode is provided. The first measurement electrode protrudes by a predetermined distance from the main body part which serves as a handle, and the person to be measured holds the main body part to press the first measurement electrode against the chest. According to the portable electrocardiographic monitor of Patent Document 1, the person to be measured holds by oneself the main body part (in a state where the hand is in contact with the second electrode), and presses the first electrode against the chest, whereby the potentials of the first electrode and the second electrode are measured. The portable electrocardiographic monitor of Patent Document 1 includes an impedance detecting circuit for detecting an impedance between the electrodes. In a case where the electrodes are not in complete contact with the skin of the person to be measured, that is, an inappropriate impedance is detected, a warning operation is performed by an LED or a warning sound is generated by a buzzer, to thereby notify the person to be measured that the contact of the electrodes is inappropriate. In other words, it is possible to detect an inappropriate impedance resulting from a poor contact of the electrodes, and when the inappropriate impedance (an inappropriate contact of the electrode) is detected, it is judged that the measurement operation is failure and a warning is generated.

SUMMARY OF THE INVENTION

Problems to be Solved by the Invention

According to the above-mentioned portable electrocardiographic monitor of Patent Document 1, a person to be measured needs to hold the main body by hands such that bioelectrical information can be obtained under a state where the first electrode is pressed against the chest. When the above-mentioned portable electrocardiographic monitor of Patent Document 1 is adopted in a case where a human body moves, it is difficult to maintain a contact state constant between the electrodes and the skin. The portable electrocardiographic monitor of this type can be used for measuring electrocardiography or the like, but is not capable of obtaining bioelectrical information under a state where a human body moves, for example, variations in electromyography while the person to be measured is playing a sport.

Also, the above-mentioned portable electrocardiographic monitor of Patent Document 1 includes only a pair of (two) electrodes, and a warning is generated for notifying a measurement failure only in the case where the impedance between the pair of (two) electrodes is inappropriate. According to the above-mentioned portable electrocardiographic monitor of Patent Document 1, it is impossible to find out which one of the two electrodes is in a state of contact failure. Accordingly, even in the case where it is detected that the impedance is inappropriate, the person to be measured cannot identify where the problem lies, that is, whether the problem lies in the way of holding the electrocardiographic monitor main body (i.e., the problem lies in a contact state between the second measurement electrode and the hand) or lies in the way of pressing the electrocardiographic monitor against the chest (i.e., the problem lies in a contact state between the first measurement electrode and the chest). According to the above-mentioned portable electrocardiographic monitor of Patent Document 1, the person to be measured is incapable of specifically knowing which one of the electrodes should be brought to an appropriate contact state so as to attain an appropriate impedance state. For this reason, it takes a long time to recover from a failure that has occurred so as to be able to resume measurement, while it is relatively less likely that the inappropriate impedance has been resolved when the measurement is resumed.

Specifically, in the case of electromyographic measurement for grasping in detail the movements of a human body in driving a car or in playing sports, it is necessary to measure electrocardiography in a plurality of muscles in general. Accordingly, it is necessary to attach pairs of electrodes (two or more electrodes) to skin surface of respective portions of the plurality of muscles which greatly move with frequency. In the electromyographic measurement, the portion of the skin to which the electrode is attached of course moves along with the movement of the muscle. Due to the movement, at least one of the plurality of electrodes often has an inappropriate attachment state (attachment is inappropriate) caused therein, or at least one of the plurality of electrodes often completely peels off. If any one of the plurality of electrodes has the inappropriate attachment caused therein, a measurement failure is caused, which makes it impossible to obtain a sufficient measurement result. Also, in the case where the measurement failure is caused, it is required to resume the measurement as soon as possible, and it is necessary to readily find, from among the plurality of electrodes, an electrode in a contact failure state and re-attach the electrode so as to be in an appropriate state. The above-mentioned portable electrocardiographic monitor basically performs measurement while having the first electrode pressed against one portion of a human body, but is incapable of measuring bioelectric signals obtained from a plurality of muscles while the human body is moving. According to the above-mentioned portable electrocardiographic monitor, which includes the means for detecting a state of contact failure as described above, it is impossible to readily find, from among the plurality of electrodes, an electrode in the state of contact failure.

In the electromyographic measurement, the distance between the centers of the two electrodes (a pair of electrodes) attached to one portion of a muscle is set to be relatively small, for example, to be less than 20 mm, in order to keep the measurement accuracy sufficient. Accordingly, the positions of the attached electrodes may be displaced along with a significant movement of the person to be measured, with the result that the electrodes come into contact with each other and are short-circuited. Patent Document 1 only refers to a problem caused in the case where the impedance is increased, while the short-circuit electrodes cannot be detected.

In view of the above-mentioned problems, the present invention has been made, and provides a bioelectrical information acquisition device and an inappropriately-attached-electrode identifying method which are capable of individually identifying, of a plurality of electrodes, an electrode which has a problem in a contact state thereof, by monitoring the contact state between the electrodes and the skin, and capable of detecting a short-circuit developed between the electrodes which causes a deterioration in measurement sensitivity, while allowing the person to be measured to be informed of a trouble during operation without any person's help.

Means for Solving the Problems

In order to solve the above-mentioned problems, the present invention provides a bioelectrical information acquisition device, which is characterized by including: at least three or more biomedical electrodes attached to a skin surface of a person to be measured for detecting bioelectrical information generated along with biological activities of the person to be measured; an acquisition section for obtaining the bioelectrical information detected; a resistance measuring section for setting a plurality of electrode pairs each constituted by two electrodes among the plurality of biomedical electrodes and measuring, for each of the electrode pairs, at least one of an electrical impedance value between two electrodes forming a pair and a resistance value between the electrodes; an attachment state judging section for judging an attachment state of each of the electrode pairs, by comparing one of the impedance value and the resistance value measured by the resistance measuring section, with a range of numeric values set in advance; and an inappropriate electrode identifying section for identifying, from among the plurality of electrode pairs, an electrode in which an inappropriate attachment state is caused, based on the attachment state judged by attachment state judging section for each of the plurality of electrode pairs.

Further, the bioelectrical information acquisition device according to the present invention preferably includes: a signal judgment section for judging whether an inappropriate attachment state is caused in at least one of the plurality of biomedical electrodes, by comparing the bioelectrical information obtained by the acquisition section with a predetermined range of numeric values; and a control section for controlling an operation of each of the acquisition section, the resistance measuring section, the attachment state judging section, the inappropriate electrode identifying section, and the signal judgment section, in which the control section preferably causes, in a case where the signal judgment section has judged that the inappropriate attachment state is caused in at least one of the plurality of biomedical electrodes, the acquisition section to stop obtaining the bioelectrical information, causes the resistance measuring section to measure at least one of the electrical impedance value and the resistance value while acquisition of the bioelectrical information is being stopped, causes the attachment state judging section to judge an attachment state of each of the electrode pairs, and causes the inappropriate electrode identifying section to identify an electrode in which an inappropriate attachment state is caused.

Still further, the bioelectrical information acquisition device according to the present invention preferably includes: a notification section for notifying, in regard to the electrode identified by the inappropriate electrode specifying section as having the inappropriate attachment state caused therein, the person to be measured of a position of the electrode.

Furthermore, the notification section preferably applies a voltage to a electrode corresponding to the identified electrode in which the inappropriate attachment state is caused so as to give an electrical stimulus from the corresponding electrode to the person to be measured, to thereby notify the person to be measured of a position of the corresponding electrode in which the inappropriate attachment state is caused.

It is also preferable that the electrode be provided with an alarming section for generating at least one of sound and light, and that the notification section operate the alarming section provided to an electrode identified by the inappropriate electrode identifying section as having the inappropriate attachment state caused therein, to thereby notify the person to be measured of a position of the electrode in which the inappropriate attachment state is caused.

The present invention also provides an inappropriately-attached-electrode identifying method for identifying an electrode in which an inappropriate attachment state is caused when detecting and obtaining bioelectrical information generated in accordance with biological activities of a person to be measured by using at least three or more biomedical electrodes attached to a skin surface of the person to be measured, the method being characterized by including the steps of: setting a plurality of electrode pairs each constituted by two electrodes of the plurality of biomedical electrodes and measuring, for each of the electrode pairs, at least one of an electrical impedance value between two electrodes forming a pair and a resistance value between the electrodes; judging an attachment state of each of the electrode pairs, by comparing one of the impedance value and the resistance value thus measured, with a range of numeric values set in advance; and identifying, from among the plurality of electrode pairs, an electrode in which an inappropriate attachment state is caused, based on each attachment state judged for each of the plurality of electrode pairs.

Note that it is preferable to perform the step of judging whether an inappropriate attachment state is caused in at least one of the plurality of biomedical electrodes, by comparing the bioelectrical information obtained with a predetermined range of numeric values, prior to the step of measuring, and in the case where it has been judged, in the step of judging, that the inappropriate attachment state is caused in at least one of the plurality of biomedical electrodes, it is preferable to stop the acquisition of the bioelectrical information and to perform the step of measuring, the step of judging, and the step of identifying, while acquisition of the bioelectrical information is being stopped.

Still further, it is preferable to include the step of notifying, in regard to the electrode identified in the step of identifying as having the inappropriate attachment state caused therein, the person to be measured of a position of the identified electrode.

Further, in the step of notifying, it is preferable to apply a voltage to an electrode identified by the notification step corresponding to the identified electrode in which the inappropriate attachment state identified in the step of identifying is caused so as to give an electrical stimulus from the predetermined electrode to the person to be measured, to thereby notify the person to be measured of a position of the electrode in which the inappropriate attachment state is caused.

It is also preferable that the electrode be provided with an alarming section for generating at least one of sound and light, and in the step of notifying, it is preferable to operate the alarming section provided to an electrode identified by the inappropriate electrode identifying section as having the inappropriate attachment state caused therein, to thereby notify the person to be measured of a position of the electrode in which the inappropriate attachment state is caused.

Effects of the Invention

According to the bioelectrical information acquisition device and the inappropriately-attached-electrode identifying method of the present invention, it is possible to readily detect an inappropriate attachment occurring in at least one of the plurality of electrodes and identify the electrode in which the inappropriate attachment has occurred. Accordingly, in the electromyographic measurement performed under a state where an inappropriate attachment such as peeling of an electrode or a short-circuit between electrodes often occurs, it is possible to speedily detect a measurement failure due to the inappropriate attachment, and to readily bring the electrode to a normal attachment state. Therefore, it is possible to significantly reduce the time necessary to recover from the inappropriate attachment of the electrode to resume the measurement. According to the bioelectrical information acquisition device and the inappropriately-attached-electrode identifying method, it is possible to obtain accurate bioelectrical information in a short period of time with fewer people.

DESCRIPTION OF SYMBOLS

| | |
|---|---|
| 10 | electromyographic measuring device 10 |
| 12 | driver |
| 13L, 13R | detection electrode pair |
| $E_{1L}, E_{2L}, E_{1R}, E_{2R}, E_3$ | electrode |
| 14 | measurement unit |
| 16 | display device |
| 20 | myopotential measuring section |
| 22 | attachment state judgment section |
| 24 | inappropriateness notifying section |
| 26 | control section |
| 32 | bio amp |
| 34 | data acquisition section |
| 36 | signal judgment section |
| 42 | impedance measuring section |
| 44 | impedance judgment section |
| 46 | inappropriate electrode identifying section |
| 62 | alarming section |

DETAILED DESCRIPTION OF THE PREFERRED EMBODIMENT

Hereinafter, a bioelectrical information acquisition device and an inappropriately-attached-electrode identifying method according to the present invention are described in detail with reference to a preferred embodiment shown in the accompanying drawings.

Figure 1:
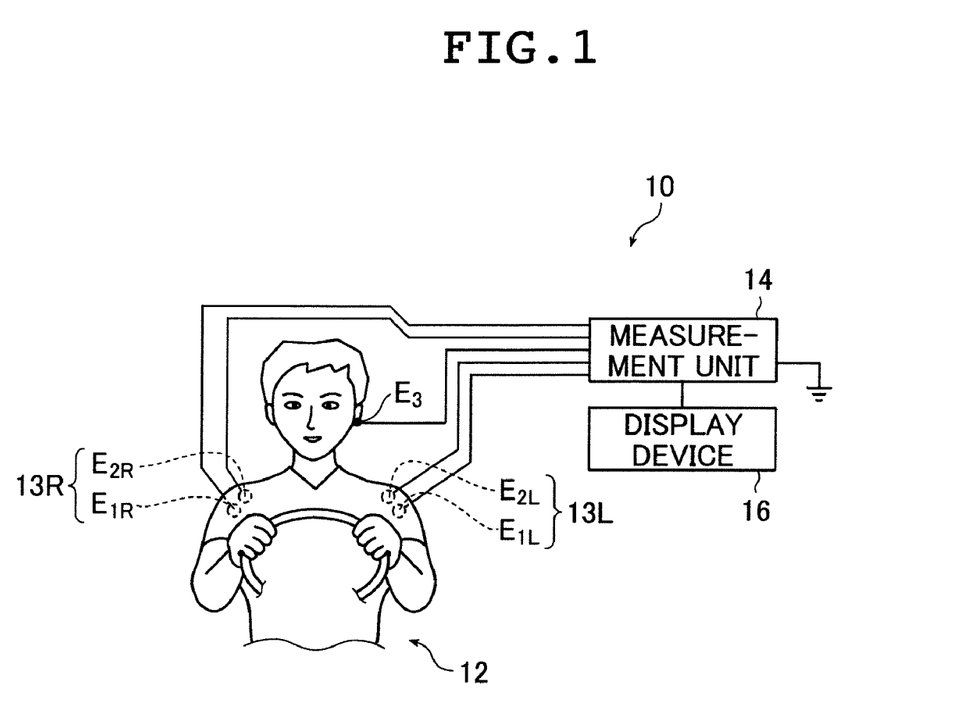
FIG. 1 is a schematic diagram showing a state where an electromyographic measuring device as an example of a bioelectrical information acquisition device according to the present invention is used to obtain electromyographic information of a driver driving a vehicle.

FIG. 1 is a schematic diagram showing a state where an electromyographic measuring device 10 (hereinafter, referred to as device 10) as an example of the bioelectrical information acquisition device according to the present invention is used to obtain electromyographic information of a driver 12 driving a vehicle. FIG. 1 shows a state where the device 10 is used to detect myopotentials of the right and left deltoid muscles of the driver 12 in time series. The device 10 is provided to a vehicle (not shown) which the driver 12 rides in and drives.

The device 10 includes a detection electrode pair 13R and a detection electrode pair 13L which are attached to the right and left shoulders of the driver 12, respectively, an electrode $E_3$ serving as a ground electrode, a measurement unit 14, and a display device 16. The detection electrode pair 13R and the detection electrode pair 13L are attached to right and left deltoid muscles of the driver 12, respectively. The detection electrode pair 13R is constituted by an electrode $E_{1R}$ and an electrode $E_{2R}$, and the detection electrode pair 13L is constituted by an electrode $E_{1L}$ and an electrode $E_{2L}$. The electrode $E_3$, which is serving as a ground electrode, is attached to one of the earlobes of the driver 12. The device 10 measures potentials of two electrodes (the electrode $E_{1L}$ and the electrode $E_{2L}$) constituting the detection electrode pair 13L, to thereby measure a myopotential of the deltoid muscles on the left shoulder of the driver. Meanwhile, the device 10 measures potentials of two electrodes (the electrode $E_{1R}$ and the electrode $E_{2R}$) constituting the detection electrode pair 13R, to thereby measure a myopotential of the deltoid muscles on the right shoulder of the driver.

Further, the device 10 measures an impedance or an electric resistance value between arbitrary two electrodes selected from among one of the two electrodes (the electrode $E_{1L}$ and the electrode $E_{2L}$) constituting the detection electrode pair 13L, one of the two electrodes (the electrode $E_{1R}$ and the electrode $E_{2R}$) constituting the detection electrode pair 13R, and the electrode $E_3$, to thereby judge whether the contact states of the selected electrodes are appropriate or not. The device 10 applies a voltage across arbitrary two electrodes of the electrodes, to thereby give an electrical stimulus to the driver 12. The electrical stimulus is mild enough that does not disturb the driving operation of the driver 12, but is strong enough that the driver 12 can recognize the electrodes across which the voltage has been applied. The display device 16 is formed of, for example, a display, which is a section for displaying a detection result of myopotentials of the left and right deltoid muscles, and attached to a position to be easily viewed by the driver 12 driving a vehicle. Hereinbelow, each section of the device 10 is described in detail.

The detection electrode pair 13L is a sensor for detecting a myopotential of the deltoid muscle of the left shoulder of the driver, and is configured by including a pair of dish-shaped electrodes of Ag/AgCL. The dish-shaped electrodes of Ag/AgCL (the electrode $E_{1L}$ and the electrode $E_{2L}$) forming a pair are attached to a surface of the left shoulder at which the deltoid muscle is located, while being separated from each other at a predetermined distance of several mm, for example, 5 mm. The detection electrode pair 13R is a sensor for detecting a myopotential of the deltoid muscle of the right shoulder of the driver, and is configured by including, similarly to the detection electrode pair 13L, a pair of dish-shaped electrodes of Ag/AgCL. The dish-shaped electrodes of Ag/AgCL (the electrode $E_{1R}$ and the electrode $E_{2R}$) forming a pair are attached to a surface of the right shoulder at which the deltoid muscle is located, while being separated from each other at a predetermined distance of several mm, for example, 5 mm.

The materials for forming the electrodes constituting one of the detection electrode pairs 13L and the 13R are not limited to Ag/AgCL, and the electrodes may be formed of another material, such as Ag or stainless steel. The electrodes are attached to a surface of the skin of the driver by using an electrode paste, after the skin is scrubbed and cleaned off with alcohol. At this time, the skin is cleaned off so as to be clean enough to have an electric resistance of 30 k$\Omega$ or less (preferably of 5 k$\Omega$). The two electrodes are attached to a center portion of the muscle to be measured, so as to be in parallel with muscle fibers. The detection electrode pair 13L and the detection electrode pair 13R are connected to a bio amp 32 (amp 32) described later of the measurement unit 14.

Meanwhile, the electrode $E_3$ is a ground electrode and attached to one of the earlobes of the driver, which is a position electrically inactive, in order to keep the potential of the driver constant. The electrode $E_3$ is provided so as to carry out the measurement with accuracy by the detection electrode pair 13L and the detection electrode pair 13R. The electrode $E_3$ is connected to the bio amp 32 (amp 32) described later of the measurement unit 14, and is grounded through the bio amp 32.

Figure 2:
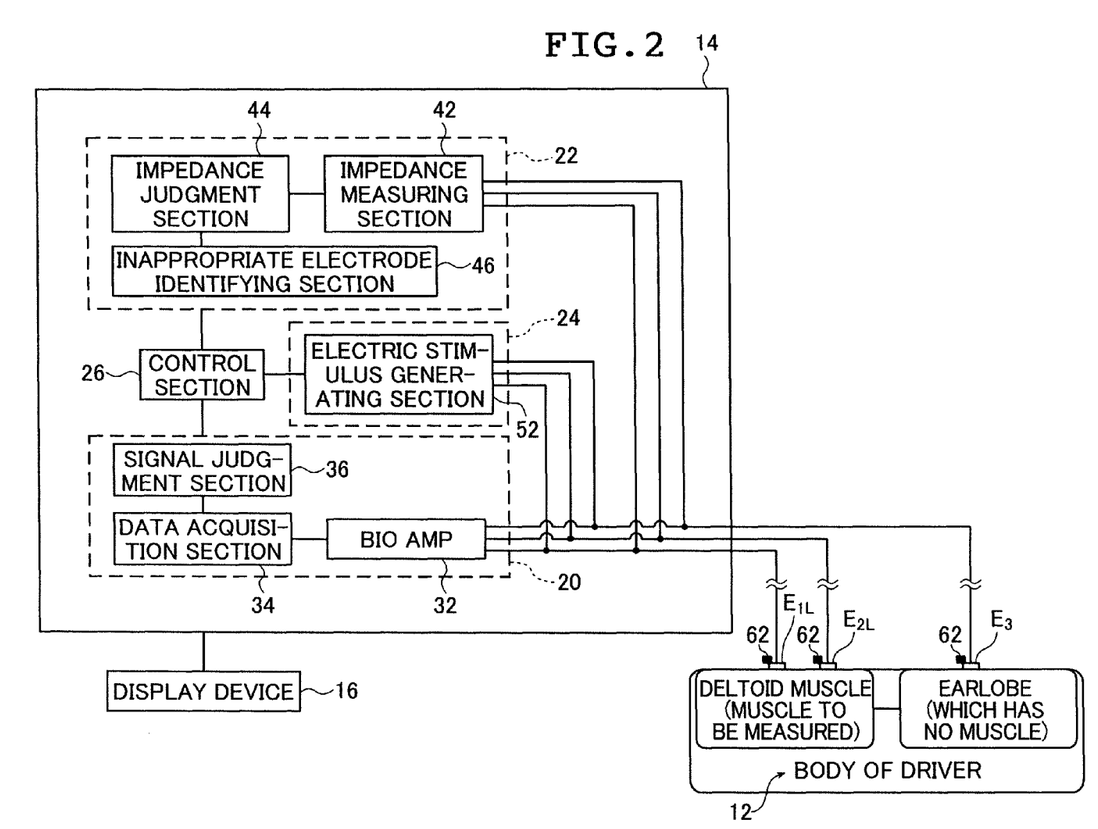
FIG. 2 is a schematic structural diagram for explaining a measurement unit of the electromyographic measuring device shown in FIG. 1.

FIG. 2 is a schematic structural diagram for explaining the measurement unit 14 of the device 10. FIG. 2 shows only one (detection electrode pair 13L) of the two detection electrode pairs 13L and 13R. The measurement unit 14 is configured by including a myopotential measuring section 20 for obtaining information on respective myopotentials of the right and left deltoid muscles of the driver 12, a judgment section 22 for measuring an impedance between arbitrary two electrodes of the electrodes so as to judge whether the attachment state of each electrode is appropriate or not, thereby identifying an electrode in which inappropriate attachment is occurring, an inappropriateness notifying section 24 for applying a voltage across arbitrary two electrodes, to thereby give an electrical stimulus to the driver 12 (the electrical stimulus being mild enough that does not disturb the driving operation of the driver 12 while strong enough that the driver 12 can recognize the electrodes across which the voltage has been applied), and a control section 26 connected to each of the myopotential measuring section 20, the judgment section 22, and the inappropriateness notifying section 24, for controlling an operation of each of the sections.

The myopotential measuring section 20, the judgment section 22, and the inappropriateness notifying section 24, of the measurement unit 14 are each connected to the two electrodes (the electrode $E_{1L}$ and the electrode $E_{2L}$) of the detection electrode pair 13L, the two electrodes (the electrode $E_{1R}$ and the electrode $E_{2R}$) of the detection electrode pair 13R, and the electrode $E_3$ serving as a ground electrode. The detection electrode pair 13L (the electrode $E_{1L}$ and the electrode $E_{2L}$) and the electrode $E_3$ form a first electrode group, and the detection electrode pair 13R (the electrode $E_{1R}$ and the electrode $E_{2R}$) and the electrode $E_3$ form a second electrode group. Each of the sections (the myopotential measuring section 20, the judgment section 22, and the inappropriateness notifying section 24) of the measurement unit 14 performs a process for each of the electrode groups. Hereinbelow, each section of the measurement unit 14 is described in detail with reference to the first electrode group, which is one of the two electrode groups. Each section of the measurement unit 14 performs the similar process for the second electrode group.

The myopotential measuring section 20 includes the bio amp 32 (amp 32) for amplifying potentials of the two electrodes (the electrode $E_{1L}$ and the electrode $E_{2L}$) of the detection electrode pair 13L (potentials of the deltoid muscle), a data acquisition section 34 for obtaining the amplified myopotential data of the deltoid muscle in time series, and a signal judgment section 36 for monitoring the time series of signals of myopotentials obtained by the data acquisition section 34 so as to judge the quality of the time series of signals obtained, to thereby judge whether or not inappropriate attachment, such as peeling of an electrode or a short-circuit between electrodes, is occurring in any of the electrodes. A feeble change in potential (several μV to several mV) derived by an electrode is amplified by the bio amp 32 by several hundred to several thousand times, so as to be a signal that can be handled by conventional electronic equipment.

The detection electrode pair 13L (the electrode $E_{1L}$ and the electrode $E_{2L}$) of the first electrode group is attached to the skin surface of the right and left shoulders of the driver 12, the shoulders frequently moving while the driver 12 is driving a vehicle. The skin surface stretches and contracts along with the movement of the right and left shoulders while the driver 12 is driving a vehicle, and therefore the electrode $E_{1L}$ and the electrode $E_{2L}$ may peel off from the skin. In addition, the distance between the electrode $E_{1L}$ and the electrode $E_{2L}$ is so narrow that it has only 5 mm as described above. For this reason, it is relatively highly likely that the electrode $E_{1L}$ and the electrode $E_{2L}$ come into contact with each other along with the movement of the shoulder, so as to be short-circuited. Further, each electrode is attached to the skin by using conductive electrode paste as described above. The distance between the electrode $E_{1L}$ and the $E_{2L}$ is originally so small that even an excess of the electrode paste that has run off to flow out around the periphery of the electrode on the skin surface leads to a short-circuit between the electrode $E_{1L}$ and the $E_{2L}$. When one of the electrodes is peeled off or the electrodes are short-circuited as described above, an inappropriateness occurs in the time series of signals of myopotentials, which makes it impossible to obtain accurate information on myopotentials.

The signal judgment section 36 monitors in real time the myopotential data of the deltoid muscle which is obtained by the data acquisition section 34 in time series order, and judges whether any failure is occurring or not in the time series data of myopotential of the deltoid muscle. In the case where the size of a noise included in the time series data of myopotential of the deltoid muscle is larger than the predetermined threshold value, the signal judgment section 36 judges that the quality of the signal is abnormal and therefore an inappropriate attachment is occurring in an electrode. Also, in the case where the occurrence frequency of a noise in the time series data of myopotential is larger than the predetermined threshold value or in the case where the level of the myopotential signal is smaller than the predetermined threshold value, the signal judgment section 36 judges that an inappropriate attachment is occurring in an electrode.

Figure 3:
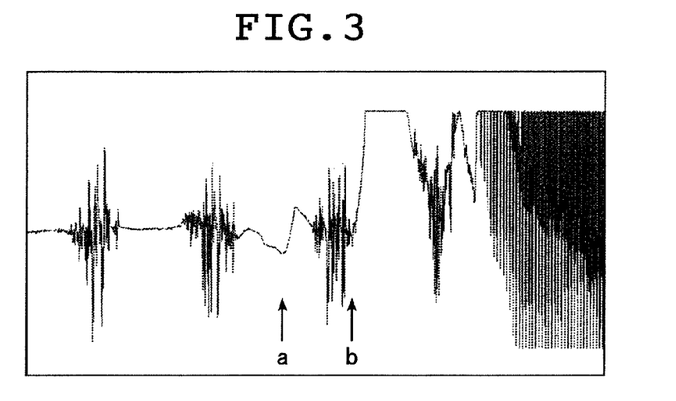
FIG. 3 is an example of the time series data of myopotential of deltoid muscles obtained by a data acquisition section of the electromyographic measuring device shown in FIG. 1.

FIG. 3 is an example of the time series data of myopotential of deltoid muscles obtained by the data acquisition section 34, which has been obtained in a case where one of the detection electrodes attached to a person to be monitored has almost peeled off once (at a point of time indicated by the arrow a) and then has completely peeled off (at a point of time indicated by the arrow b). As can be seen from FIG. 3, the measurement data is greatly disturbed at the same time when one of the electrodes peels off, and the signal level fluctuates extremely up and down. The range (normal range) may be set in advance for the level of the myopotential signal, and in the case where the level of the myopotential signal falls out of the normal range, the signal judgment section 36 may judge that an inappropriate attachment is occurring in an electrode.

Accurate measurement cannot be performed by obtaining the myopotential data under the state where an inappropriate attachment is occurring as described above. In the case where it has been judged that an inappropriate attachment is occurring in an electrode, it is desired that the electrode with the inappropriate attachment be identified as soon as possible, the electrode be re-attached in a normal state, and the myopotential measurement be resumed. In the case where the signal judgment section 36 has judged that an inappropriate attachment is occurring in an electrode, the control section 26 shuts down an input of the electromyography to the bio amp 32, to thereby temporarily suspend the measurement operation which is being performed inaccurately.

The control section 26 then causes the judgment section 22 to measure an impedance between respective combinations of two of the three electrodes of the first electrode group, to thereby judge whether each one of the three electrodes (the electrode $E_{1L}$, the electrode $E_{2L}$, and the electrode $E_3$) of the first electrode group is appropriately attached or not.

Figure 4A:
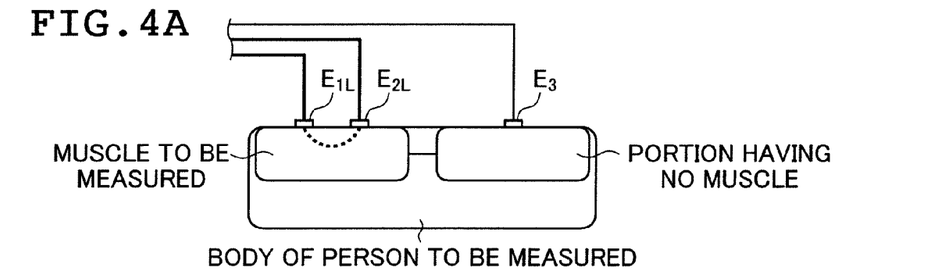
FIG. 4 is a schematic diagram for explaining various combinations of the electrodes, for each of which an impedance is measured by an impedance measuring section of the electromyographic measuring device shown in FIG. 1.
Figure 4B:
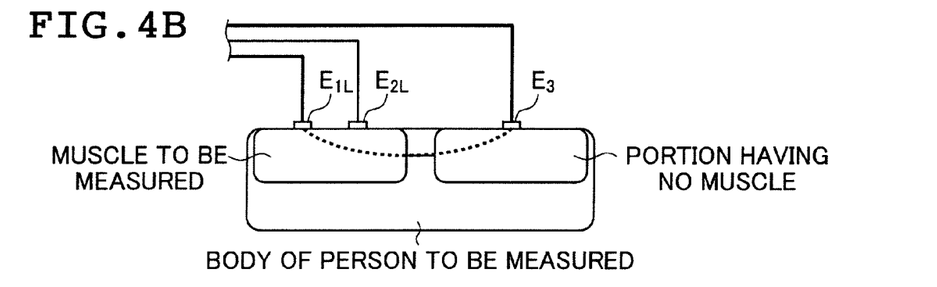
Figure 4C:
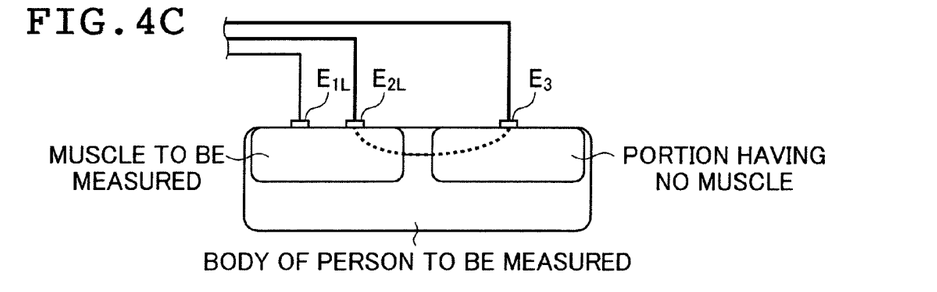

The judgment section 22 includes an impedance measuring section 42, an impedance judgment section 44, and an inappropriate electrode identifying section 46. The impedance measuring section 42 sets all the combinations of two different electrodes of the three electrodes of the first electrode group, the two different electrodes constituting each of the set electrode pairs, and measures an impedance of the two electrodes of each set electrode pair. FIG. 4 is a schematic diagram for explaining respective combinations of the electrodes, for each of which an impedance is measured in the impedance section 42. In the case of the first electrode group, an impedance between the electrode $E_{1L}$ and the electrode $E_{2L}$ of FIG. 4(a), an impedance between the electrode $E_{1L}$ and the electrode $E_3$ of FIG. 4(b), and an impedance between the electrode $E_{2L}$ and the electrode $E_3$ of FIG. 4(c) are respectively measured. The impedance measuring section 42 is known as impedance measuring means for measuring an impedance between the two electrodes by applying an alternating voltage to a pair of the electrodes (two electrodes) having an impedance to be measured, to thereby obtain the impedance thereof. According to the bioelectrical information acquisition device of the present invention, in order to judge whether each electrode is appropriately attached, the judgment section 22 measures an impedance between arbitrary two electrodes of the electrodes. However, the present invention is not limited to this. The judgment section 22 may measure an electric resistance between arbitrary two electrodes of the electrodes to thereby judge whether each electrode is appropriately attached. In this case, a direct voltage may be applied to a pair of the electrodes (two electrodes) having a resistance to be measured, to thereby obtain the electric resistance between the two electrodes.

The impedance judgment section 44 has ranges (normal ranges) of numeric values of impedances, which would be measured when all the electrodes are normally attached, for respective electrode pairs each constituted by two electrodes, the ranges being preset for each pair. The impedance judgment section 44 compares each impedance measured by the impedance measuring section 42 for each electrode pair, with the range of the numeric value which is preset for each pair, to thereby judge whether or not the impedance of each electrode pair falls within the range of the numeric value. For example, in the case where at least one of the two electrodes is about to peel off from the skin, the impedance increases to exceed the normal range. Further, in the case where the electrode peels off from the skin, the impedance increases to be excessively large, making the measurement impossible. Alternatively, in the case where the two detection electrodes attached to the skin as being adjacent to each other come into contact with each other and the electrodes are short-circuited, the impedance decreases to be excessively small.

The inappropriate electrode identifying section 46 receives the results of the judgment made by the impedance judgment section 44 for respective electrode pairs, and identifies the electrode in which an inappropriate attachment is occurring based on the results of the judgment made for the plurality of pairs, while specifying how the electrode thus identified is attached. The inappropriate electrode identifying section 46 compares the results of the judgment made by the impedance judgment section 44 for respective electrode pairs with, for example, a reference table shown in below as a table 1 which is stored in advance, to thereby identify the electrode in which an inappropriate attachment is occurring while specifying how the electrode thus identified is attached.

TABLE 1

| | Case 1 | Case 2 | Case 3 | Case 4 | Case 5 | Electrode pair to be judged |
|---|---|---|---|---|---|---|
| Impedance judgment result | o | o | Excessively large | Excessively large | Excessively small | $E_{1L}$-$E_{2L}$ |
| | o | Excessively large | o | Excessively large | o | $E_3$-$E_{1L}$ |
| | o | Excessively large | Excessively large | o | o | $E_3$-$E_{2L}$ |
| Inappropriate electrode identification result | All normal | Peeled off $E_3$ | Peeled off $E_2$ | Peeled off $E_1$ | Short-circuited (between $E_{1L}$ and $E_{2L}$) | |
| Electrodes to be applied with a voltage | None | $E_1$-$E_2$ | $E_1$-$E_3$ | $E_2$-$E_3$ | $E_1 \cdot E_2$-$E_3$ | |

In the state where the signal judgment section 36 has judged that an inappropriateness is occurring in the time series data of myopotentials of the deltoid muscle, five cases as shown in the table 1 are conceivable as combinations of attachment states of the electrodes in the first electrode group. In the table 1, "O" indicates a case where an impedance is normal. Specifically, the five cases include a case (case 1) where all the electrodes (the electrode $E_{1L}$, the electrode $E_{2L}$, the electrode $E_3$) in the first electrode group are normally attached, respective cases (case 2 to case 4) where any one of the electrodes in the first electrode group has peeled off, and a case (case 5) where the electrode $E_{1L}$ and the electrode $E_{2L}$ in the detection electrode pair 13L contact with each other to be short-circuited. The inappropriate electrode identifying section 46 specifies which of the five cases applies to the attachment state of each electrode in the first electrode group, with reference to correspondence information stored in advance as shown in the table 1. In the case where it has been judged that the case 1 applies to every attachment state of each electrode, it is possible to judge that the inappropriateness in the measurement signal is caused by another factor. In this case, attachment of a voltage by the inappropriateness notifying section 24 of the inappropriateness notifying section 24, which is described later, is not performed.

In the electromyographic measurement, the following case can be assumed, where two of the electrodes of the three electrodes constituting the first electrode group peel off. According to this embodiment, however, the signal judgment section 36 successively monitors the quality of the electromyographic measurement data. Accordingly, it is possible to readily identify with accuracy, by referring to the table 1, an electrode in which an inappropriateness has occurred, without waiting for another electrode to have an inappropriate attachment state, that is, at a point of time when an inappropriate attachment occurs in any one of the three electrodes.

When the inappropriate electrode identifying section 46 identifies an electrode in which an inappropriate attachment is occurring, an electric stimulus generating section 52 of the inappropriateness notifying section 24 applies a predetermined voltage to a electrode corresponding to the electrode identified as having an inappropriate attachment occurring therein. In this manner, an electric stimulus is applied to a portion (portion corresponding to the electrode which has been identified as having an inappropriate attachment is occurring therein) of a body of the driver 12, as shown in the table 1. The driver 12 can recognize which one of the plurality of electrodes attached to one's own body is having an inappropriate attachment occurring therein, based on the portion having received the electric stimulus. For example, in the case 4, a low-frequency voltage is applied to each of a portion where the electrode $E_{2L}$ is attached and a portion (an earlobe) where the electrode $E_3$ is attached, and the driver 12 feels a stimulus at each of those portions. Accordingly, the driver 12 learns that the electrodes on the portions having received the stimuli are attached while the electrode $E_{1L}$ which has received no stimulus has an inappropriate attachment occurring therein. According to the bioelectrical information acquisition device of the present invention, even in the case where an inappropriate attachment has occurred in an electrode, the driver 12 can readily identify the electrode in which the inappropriate attachment has occurred.

It should be noted that, in the bioelectrical information acquisition device of the present invention, a mechanism for notifying a person to be measured, such as a driver, of which one of the electrodes has an inappropriate attachment occurring therein is not limited to a configuration in which an electric stimulus is given to the body of the driver 12. For example, each electrode may be provided with an alarming section 62 (see FIG. 2) including a buzzer or light emitting means (such as an LED), and the alarming section 62 provided to each electrode may be operated only in an electrode in which an inappropriate attachment has occurred. In this manner, the driver 12 can readily learn that an inappropriate attachment has occurred in an electrode provided with the alarming section which has operated. In this case, for example, an alarming section provided to each electrode may be connected to the inappropriateness notifying section 24 of the measurement unit through a power supply wire different from a signal line connecting each electrode and the bio amp or a signal line connecting each electrode and the impedance measuring section, such that an operation voltage may be applied, by the inappropriateness notifying section, only to an alarming section provided to an electrode, which has been identified by the inappropriate electrode identifying section 46 and in which the inappropriate attachment is occurring.

Information including the time series of signals of myopotentials obtained by the data acquisition section 34, the judgment result in the signal judgment section 36, and results obtained in each section of the judgment section 22 is displayed on a screen of the display device 16 serving as a display, so as to be fully confirmed by the driver 12.

In the above, the electromyographic measuring device 10 as an example of the bioelectrical information acquisition device according to the present invention has been described. The attachment of the bioelectrical information acquisition device of the present invention is not limited to the measurement of the myopotential data of a deltoid muscle of a driver. The muscle of a person to be measured for measuring myopotentials is not specifically limited, and a type of work to be performed by the person to be measured is not specifically limited either. By using the bioelectrical information acquisition device of the present invention, it is possible to identify, from among a plurality of electrodes attached to a body of a person to be measured, an electrode having an attachment failure, at a point of time when the attachment failure occurs in one of the plurality of electrodes. The bioelectrical information acquisition device of the present invention can be suitably adopted in the electromyographic measurement, such as an electromyographic measurement for learning movements of a human body in detail in sporting activities, in which a large number of, for example, several tens of electrodes are attached to a body of a person to be measured to measure electromyography.

Figure 5:
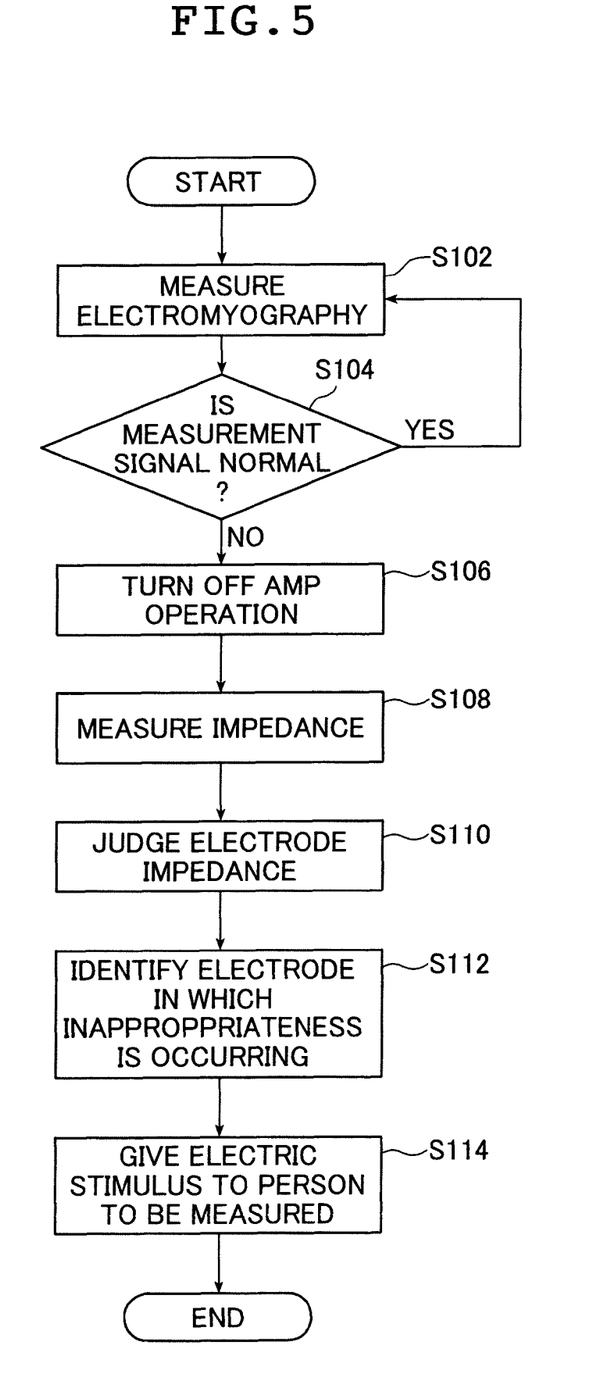
FIG. 5 shows a flowchart indicating an operation of the electromyographic measuring device shown in FIG. 1, which is an example of an inappropriately-attached-electrode identifying method according to the present invention, the flowchart showing an operation starting from measuring electromyographic information on a driver driving a vehicle to identifying an electrode in which an inappropriate attachment is occurring.

FIG. 5 shows a flowchart indicating an example of an inappropriately-attached-electrode identifying method according to the present invention, the flowchart showing an operation of the device 10. The flowchart of FIG. 5 shows an operation starting from measuring electromyographic information on the driver 12 driving a vehicle to identifying an electrode in which an inappropriate attachment is occurring. In the following, identifying process of the electromyographic measurement and the inappropriate attachment in an electrode in the first electrode group shown in FIG. 2 is described in detail. In the following, a process operation relating to the first electrode group, which is one of the two electrode groups, is described in detail. The device 10 performs a similar operation for the second electrode group.

When the electromyographic measurement is started for the driver 12, the myopotential measuring section 20 starts measuring myopotential data of the driver 12 (Step S102). In the myopotential measurement, potentials (myopotentials of a deltoid muscle) of the two electrodes (the electrode $E_{1L}$ and the electrode $E_{2L}$) of the detection electrode pair 13L are amplified by the bio amp 32 (amp 32), and the data acquisition section 34 obtains the amplified myopotential data of the deltoid muscle in time series, to thereby perform the myopotential measurement. During the myopotential measurement, the data acquisition section 34 monitors time series of signals of myopotentials thus obtained, and judges the quality of the time series of signals thus obtained, to thereby judge whether or not an inappropriate attachment, such as peel-off of an electrode or a short-circuit between electrodes, is occurring in an electrode (Step S104). The signal judgment section 36 monitors in real time the myopotential data of the deltoid muscle obtained in time series by the data acquisition section 34, and successively judges whether or not inappropriateness is occurring in the measurement signals.

In the case where it has been judged that an inappropriate attachment is occurring in an electrode in Step S106, the control section 26 turns OFF the bio amp 32 to shut off an input of the electromyography to the bio amp 32, to thereby temporarily suspend the electromyographic measurement (Step S106). Then, the control section 26 causes the judgment section 22 to measure an impedance of each combination of the two electrodes of the three electrodes in the first electrode group (Step S108), and to judge whether the contact state of each of the three electrodes (the electrode $E_{1L}$, the electrode $E_{2L}$, and the electrode $E_3$) of the first electrode group is appropriate or not (Step S110).

In Step S108, the impedance measurement section 42 sets every combination for an electrode pair constituted by two different electrodes of the three electrodes in the first electrode group, and measures an impedance between the two electrodes constituting each electrode pair. Then, in Step S110, the impedance judgment section 44 compares the impedance between the two electrodes measured for each pair in Step S108 with a range of numeric values set in advance for each pair, to thereby judge whether or not the impedance between electrodes of each pair falls within the range of numeric values.

Then, the inappropriate electrode identifying section 46 receives a result obtained in the impedance judgment section 44 for each pair, and identifies, based on the results for the plurality of pairs, an electrode in which an inappropriate attachment is occurring while specifying how the electrode thus identified is attached (Step S112).

When an electrode in which an inappropriate attachment is occurring is specified in Step S112, the control section 26 applies a predetermined voltage to an electrode corresponding to the electrode identified as having an inappropriate attachment occurring therein, to thereby give an electric stimulus to a predetermined portion (a portion corresponding to the electrode identified as having an inappropriate attachment occurring therein) of a body of the driver 12 (Step S114). The driver 12 can recognize which one of the plurality of electrodes attached to one's own body is having an inappropriate attachment occurring therein, based on the portion having received the electric stimulus. By adopting the bioelectrical information acquisition device of the present invention, a person to be measured, such as the driver 12, can learn by oneself that an inappropriate attachment is occurring in an electrode during the measurement of bioelectrical information such as electromyography or electrocardiography. Further, an electrode in which an inappropriate attachment has occurred can be readily identified, from among a plurality of electrodes. According to the bioelectrical information acquisition device of the present invention, it is possible to readily detect the inappropriate attachment occurring in an electrode and identify the electrode in which the inappropriate attachment has occurred. Accordingly, in the electromyographic measurement performed under a state where an inappropriate attachment such as peel-off of an electrode or a short-circuit between electrodes often occurs, it is possible to speedily detect a measurement failure due to the inappropriate attachment, and to readily bring the electrode to a normal attachment state. Therefore, it is possible to significantly reduce the time necessary to recover from the inappropriate attachment of the electrode to resume the measurement. According to the bioelectrical information acquisition device and the inappropriately-attached-electrode identifying method of the present invention, it is possible to obtain accurate bioelectrical information in a short period of time with fewer people.

In the above, the bioelectrical information acquisition device and the inappropriately-attached-electrode identifying method have been described in detail. However, the present invention is not limited to the above-mentioned embodiment, and it is of course possible to make various improvements and modifications thereto without departing from the gist of the present invention.

What is claimed is:

1. A bioelectrical information acquisition device comprising:
   three or more electrodes including a plurality of biomedical electrodes attached to a skin surface of a person to be measured for monitoring a bioelectrical information, the bioelectrical information generated along with biological activities of the person;
   an acquisition section for acquiring the monitored bioelectrical information;
   a resistance measuring section for setting a plurality of electrode pairs, each pair constituted by two electrodes of the three or more electrodes and measuring at least one of an electrical impedance value and a resistance value between two electrodes forming each of the electrode pairs,
   an attachment state judging section for judging an attachment state of each of the electrode pairs, by comparing the impedance value or the resistance value measured by the resistance measuring section, with a predetermined range of numeric values; and
   an inappropriate electrode identifying section for identifying an electrode in an inappropriate attachment state from the plurality of electrode pairs based on the attachment state of each of the plurality of electrode pairs, the attachment state judged by attachment state judging section; and
   a notification section for notifying the person to be measured of the electrode in the inappropriate attachment state identified by the inappropriate electrode identifying section,
   wherein the notification section is configured to give an electrical stimulus from each electrode of specified electrode pairs to the skin surface of the person to be measured by applying a voltage to each electrode of the specified electrode pairs, the specified electrode pairs determined in accordance with the electrode in the inappropriate attachment state identified by the inappropriate electrode identifying section, to thereby notify the person to be measured of an electrode from which the electrical stimulus has not been given to the skin surface of the person as the electrode in the inappropriate attachment state.

2. The bioelectrical information acquisition device according to claim 1, further comprising:
   a signal judgment section for judging whether the inappropriate attachment state occurs in at least one of the plurality of electrodes, by comparing the bioelectrical information acquired by the acquisition section with a predetermined range of numeric values; and
   a control section for controlling an operation of each of the acquisition section, the resistance measuring section, the attachment state judging section, the inappropriate electrode identifying section, and the signal judgment section;
   wherein the control section is configured to cause the acquisition section to stop acquiring the bioelectrical information, in a case where the signal judgment section has judged that the inappropriate attachment state occurs in at least one of the plurality of electrodes,
   the control section is configured to cause the resistance measuring section to measure at least one of the electrical impedance value and the resistance value,
   the control section is configured to cause the attachment state judging section to judge the attachment state of each of the electrode pairs, and
   the control section is configured to cause the inappropriate electrode identifying section to identify an electrode in the inappropriate attachment state, while acquiring the bioelectrical information is being stopped.

3. The bioelectrical information acquisition device according to claim 1, further comprising an alarming section for generating at least one of sound and light, the alarming section provided to each of the electrodes;
   wherein the notification section operates an alarming section provided to the electrode in the inappropriate attachment state to thereby notify the person to be measured of the electrode in the inappropriate attachment state, the electrode in the inappropriate attachment state identified by the inappropriate electrode identifying section.

4. The bioelectrical information acquisition device according to claim 1, wherein the resistance measuring section is configured to set sets the plurality of electrodes pairs with respect to all combinations of two electrodes different from each other in the three or more electrodes.

5. The bioelectrical information acquisition device according to claim 1, wherein the three or more electrodes constitute at least one electrode group, each group comprising three electrodes containing a pair of biomedical electrodes attached to the skin surface of a respective portion of a moving muscle of the person to be measured under activities for monitoring the bioelectrical information and a ground electrode attached to the skin surface of a portion not corresponding to the respective portion of the moving muscle, the bioelectrical information being a myopotential generated in the respective portion of the moving muscle in response to the activities of the person,
   the resistance measuring section configured to set three electrode pairs containing an electrode pair of the pair of biomedical electrodes, electrode pair consisting of one electrode of the pair of biomedical electrodes and the ground electrode and an electrode pair consisting of another electrode of the pair of biomedical electrodes and the ground electrode, in each electrode group and to measure measures at least one of the electrical impedance value and the resistance value between two electrodes forming each of the three electrode pairs of the electrode group,
   the attachment state judging section configured to judge the attachment state of each of the three electrode pairs of the electrode group, by comparing the impedance value or the resistance value between the two electrodes forming each of the electrode pairs of the electrode group measured by the resistance measuring section, with the predetermined range of the numeric values, and
   the inappropriate electrode identifying section configured to identify as the electrode in the inappropriate attachment state an electrode in the three electrodes in the electrode group that is not one of the two electrodes of the electrode pair the attachment states of which have been judged as being an appropriate attachment state by said attachment state judging section.

6. The bioelectrical information acquisition device according to claim 5,
   wherein said notification section is configured to give an electrical stimulus from remainder two electrodes to the person to be measured by applying a voltage to the remainder two electrodes, the remainder two electrodes being the other electrodes of the electrode group containing the electrode in the inappropriate attachment state identified by the inappropriate electrode identifying section, to thereby notify the person to be measured of the electrode from which the electrical stimulus has not been given as the electrode in the inappropriate attachment state.

7. An inappropriately-attached-electrode identifying method for identifying an electrode in an inappropriate attachment state when monitoring and acquiring bioelectrical information, the bioelectrical information generated in accordance with biological activities of a person to be measured by using three or more electrodes including a plurality of biomedical electrodes attached to a skin surface of the person to be measured, comprising the steps of:

setting a plurality of electrode pairs, each pair constituted by two electrodes of the three or more electrodes and measuring at least one of an electrical impedance value and a resistance value between the two electrodes forming each of the electrode pairs;

judging an attachment state of each of the electrode pairs, by comparing the impedance value or the resistance value thus measured, with a predetermined range of numeric values;

identifying an electrode in an inappropriate attachment state from the plurality of electrode pairs based on the judged attachment state of each of the plurality of electrode pairs; and notifying the person to be measured of an electrode in the inappropriate attachment state identified in the identifying step, wherein in the notifying step, the person to be measured is notified of an electrode from which the electrical stimulus has not been given to the skin surface of the person as the electrode in the inappropriate attachment state by giving an electrical stimulus to the skin surface of the person to be measured from each electrode of specified electrode pairs, the electrical stimulus given by applying a voltage to each electrode of the specified electrode pairs, the specified electrode pairs being determined in accordance with the electrode in the inappropriate attachment state identified in the identifying step.

8. The inappropriately-attached-electrode identifying method according to claim 7, further comprising the steps of:

judging whether an inappropriate attachment state occurs in at least one of the plurality of electrodes, by comparing the bioelectrical information obtained with a predetermined range of numeric values, prior to the measuring, stopping the acquiring of the bioelectrical information, in the case where it has been judged that the inappropriate attachment state occurs in at least one of the plurality of electrodes in the judging, performing the judging and the identifying, while the acquiring of the bioelectrical information is being stopped.

9. The inappropriately-attached-electrode identifying method according to claim 7, wherein each of the electrodes comprises an alarming section for generating at least one of sound and light;

wherein in the notifying step, the person to be measured is notified of the electrode in the inappropriate attachment state by operating the alarming section of the electrode in the inappropriate attachment state, the electrode in the inappropriate attachment state identified in the identifying step.

10. The inappropriately-attached-electrode identifying method according to claim 7, wherein in the measuring step, the plurality of electrode pairs are set with respect to all combinations of two electrodes different from each other in the three or more electrodes.

11. The inappropriately-attached-electrode identifying method according to claim 7, wherein the three or more electrodes constitute at least one electrode group, each group comprising three electrodes containing a pair of biomedical electrodes attached to the skin surface of a respective portion of a moving muscle of the person to be measured under activities for monitoring the bioelectrical information and a ground electrode attached to the skin surface of a portion not corresponding to the respective portion of the moving muscle, the bioelectrical information being a myopotential generated in the respective portion of the moving muscle in response to the activities of the person, the measuring step sets three electrode pairs containing an electrode pair of the pair of the biomedical electrodes, an electrode pair consisting of one electrode of the pair of the biomedical electrodes and the ground electrode and an electrode pair consisting of another electrode of the pair of biomedical electrodes and the ground electrode, in each electrode group and measuring at least one of the electrical impedance value and the resistance value between the two electrodes forming each of the three electrode pairs of the electrode group, the judging step judges the attachment state of each of the three electrode pairs of the electrode group, by comparing the impedance value or the resistance value between the two electrodes forming each of the electrode pairs of the electrode group measured by the measuring step, with the predetermined range of the numeric values, and the identifying step identifies an electrode as being in the inappropriate attachment state when said electrode in the three electrodes in the electrode group that is not included the electrode pair the attachment states of which have been judged as being an appropriate attachment state by the judging step.

12. The inappropriately-attached-electrode identifying method according to claim 11, wherein the notifying step gives an electrical stimulus from remainder two electrodes to the person to be measured by applying a voltage to the remainder two electrodes, the remainder two electrodes being the other electrodes of the electrode group containing the electrode in the inappropriate attachment state identified by the identifying step, to thereby notify the person to be measured of the electrode from which the electrical stimulus has not been given as the electrode in the inappropriate attachment state.

* * * * *